US008845670B2

(12) United States Patent  
Smith

(10) Patent No.: US 8,845,670 B2  
(45) Date of Patent: Sep. 30, 2014

(54) TROCAR ASSEMBLY WITH OBTURATOR DESIGN

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 235 days.

(21) Appl. No.: 12/513,466

(22) PCT Filed: Dec. 14, 2007

(86) PCT No.: PCT/US2007/025568
§ 371 (c)(1),
(2), (4) Date: May 4, 2009

(87) PCT Pub. No.: WO2008/076340
PCT Pub. Date: Jun. 26, 2008

(65) Prior Publication Data
US 2010/0076478 A1  Mar. 25, 2010

Related U.S. Application Data

(60) Provisional application No. 60/875,151, filed on Dec. 15, 2006.

(51) Int. Cl.
*A61B 17/34* (2006.01)
*A61B 19/00* (2006.01)
*A61B 17/32* (2006.01)
*A61B 17/00* (2006.01)

(52) U.S. Cl.
CPC ......... *A61B 17/3417* (2013.01); *A61B 19/5212* (2013.01); *A61B 2017/320044* (2013.01); *A61B 2017/346* (2013.01); *A61B 2017/3454* (2013.01); *A61B 2017/0046* (2013.01); *A61B 2017/00477* (2013.01)
USPC ........................................................ 606/185

(58) Field of Classification Search
CPC ............................................. A61B 2017/3454
USPC ........... 606/185, 184; 433/102; 604/506, 264, 604/174
See application file for complete search history.

(56) References Cited

U.S. PATENT DOCUMENTS 4,535,773 A  8/1985 Yoon
4,601,710 A  7/1986 Moll (Continued)

FOREIGN PATENT DOCUMENTS

EP  0 604 197 A2  6/1994
EP  1 712 196 A2  10/2006

(Continued)

OTHER PUBLICATIONS

International Search Report for PCT/US07/25568—date of mailing is Jun. 5, 2008 (3 pages).

(Continued)

*Primary Examiner* — Kathleen Holwerda
*Assistant Examiner* — Sarah Simpson

(57) ABSTRACT

An obturator for use in penetrating tissue includes an elongate member defining a longitudinal axis, and having a proximal end and a distal end, and a penetrating member adjacent the distal end of the elongate member. The penetrating member has a distal penetrating tip dimensioned to pass through tissue. The penetrating member defines an external wall leading toward the penetrating tip. The external wall includes a plurality of raised elements extending at least radially outwardly relative to the longitudinal axis and being in general longitudinal alignment. Adjacent raised elements are spaced along the longitudinal axis to thereby accommodate tissue displaced during passage of the penetrating member through tissue. The raised elements are dimensioned to be generally atraumatic to tissue. The raised elements may define an arcuate profile.

26 Claims, 5 Drawing Sheets

(56) References Cited

U.S. PATENT DOCUMENTS

| | | | |
|---|---|---|---|
| 4,654,030 A | 3/1987 | Moll et al. | |
| 5,066,288 A | 11/1991 | Deniega et al. | |
| 5,104,382 A | 4/1992 | Brinkerhoff et al. | |
| 5,215,526 A | 6/1993 | Deniega et al. | |
| 5,224,952 A | 7/1993 | Deniega et al. | |
| 5,226,891 A | 7/1993 | Bushatz et al. | |
| 5,232,440 A | 8/1993 | Wilk | |
| 5,248,298 A | 9/1993 | Bedi et al. | |
| 5,271,380 A * | 12/1993 | Riek et al. | 600/104 |
| 5,314,417 A | 5/1994 | Stephens et al. | |
| 5,364,372 A | 11/1994 | Danks et al. | |
| 5,366,445 A | 11/1994 | Haber et al. | |
| 5,372,588 A | 12/1994 | Farley et al. | |
| 5,387,197 A | 2/1995 | Smith et al. | |
| 5,399,167 A | 3/1995 | Deniega | |
| 5,411,515 A | 5/1995 | Haber et al. | |
| 5,471,705 A | 12/1995 | Dao | |
| 5,478,317 A | 12/1995 | Yoon | |
| 5,487,745 A | 1/1996 | McKenzie | |
| 5,522,833 A | 6/1996 | Stephens et al. | |
| 5,533,977 A | 7/1996 | Metcalf et al. | |
| 5,538,509 A | 7/1996 | Dunlap et al. | |
| 5,545,150 A | 8/1996 | Danks et al. | |
| 5,554,137 A | 9/1996 | Young et al. | |
| 5,554,167 A | 9/1996 | Young et al. | |
| 5,569,160 A | 10/1996 | Sauer et al. | |
| 5,607,440 A | 3/1997 | Danks et al. | |
| 5,609,604 A | 3/1997 | Schwemberger et al. | |
| 5,624,459 A | 4/1997 | Kortenbach et al. | |
| 5,658,236 A | 8/1997 | Sauer et al. | |
| 5,669,885 A | 9/1997 | Smith | |
| 5,676,156 A | 10/1997 | Yoon | |
| 5,685,820 A | 11/1997 | Riek et al. | |
| 5,690,663 A | 11/1997 | Stephens | |
| 5,690,664 A | 11/1997 | Sauer et al. | |
| 5,697,913 A | 12/1997 | Sierocuk et al. | |
| 5,709,671 A | 1/1998 | Stephens et al. | |
| 5,772,660 A | 6/1998 | Young et al. | |
| 5,776,112 A | 7/1998 | Stephens et al. | |
| 5,797,943 A | 8/1998 | Danks et al. | |
| 5,824,002 A | 10/1998 | Gentelia et al. | |
| 5,827,315 A | 10/1998 | Yoon | |
| 5,843,115 A | 12/1998 | Morejon | |
| 5,860,996 A | 1/1999 | Urban et al. | |
| 5,868,773 A | 2/1999 | Danks et al. | |
| 5,879,332 A | 3/1999 | Schwemberger et al. | |
| 5,893,369 A | 4/1999 | LeMole | |
| 5,904,699 A | 5/1999 | Schwemberger et al. | |
| 5,913,848 A | 6/1999 | Luther et al. | |
| 5,916,232 A | 6/1999 | Hart | |
| 5,947,930 A | 9/1999 | Schwemberger et al. | |
| 5,980,493 A | 11/1999 | Smith et al. | |
| 5,984,941 A | 11/1999 | Wilson et al. | |
| 5,997,510 A | 12/1999 | Schwemberger | |
| 6,017,356 A | 1/2000 | Frederick et al. | |
| 6,022,367 A | 2/2000 | Sherts | |
| 6,030,402 A | 2/2000 | Thompson et al. | |
| 6,036,657 A | 3/2000 | Milliman et al. | |
| 6,063,099 A | 5/2000 | Danks et al. | |
| 6,228,058 B1 | 5/2001 | Dennis et al. | |
| 6,319,226 B1 | 11/2001 | Sherry | |
| 6,497,687 B1 | 12/2002 | Bianco | |
| 6,497,716 B1 | 12/2002 | Green et al. | |
| 6,544,277 B1 | 4/2003 | O'Heeron et al. | |
| 6,613,063 B1 | 9/2003 | Hunsberger | |
| 6,656,198 B2 | 12/2003 | Tsonton et al. | |
| 6,685,630 B2 | 2/2004 | Sauer et al. | |
| 6,716,201 B2 | 4/2004 | Bianco | |
| 6,719,746 B2 | 4/2004 | Bianco | |
| 6,830,578 B2 | 12/2004 | O'Heeron et al. | |
| 6,835,201 B2 | 12/2004 | O'Heeron et al. | |
| 6,837,874 B1 | 1/2005 | Popov | |
| 6,960,164 B2 | 11/2005 | O'Heeron | |
| D518,177 S | 3/2006 | Bianco | |
| 7,018,205 B2 * | 3/2006 | Abel | 433/102 |
| D531,726 S | 11/2006 | Bianco et al. | |
| 7,168,952 B2 * | 1/2007 | Karmaker et al. | 433/224 |
| 7,320,694 B2 | 1/2008 | O'Heeron | |
| 7,344,519 B2 | 3/2008 | Wing et al. | |
| 7,758,603 B2 | 7/2010 | Taylor et al. | |
| 2002/0183775 A1 * | 12/2002 | Tsonton et al. | 606/185 |
| 2003/0100914 A1 | 5/2003 | O'Heeron et al. | |
| 2003/0109894 A1 | 6/2003 | Bianco | |
| 2004/0015182 A1 | 1/2004 | Kieturakis et al. | |
| 2004/0199121 A1 * | 10/2004 | Wenchell et al. | 604/167.06 |
| 2004/0230155 A1 | 11/2004 | Bianco et al. | |
| 2004/0230217 A1 | 11/2004 | O'Heeron et al. | |
| 2005/0033304 A1 | 2/2005 | O'Heeron | |
| 2005/0038466 A1 | 2/2005 | O'Heeron et al. | |
| 2005/0065543 A1 | 3/2005 | Kahle et al. | |
| 2005/0107816 A1 * | 5/2005 | Pingleton et al. | 606/185 |
| 2005/0119676 A1 | 6/2005 | Bumbalough et al. | |
| 2005/0203559 A1 | 9/2005 | O'Heeron | |
| 2005/0209623 A1 | 9/2005 | Patton | |
| 2005/0261717 A1 | 11/2005 | Sauer et al. | |
| 2006/0008766 A1 * | 1/2006 | Fischer | 433/102 |
| 2006/0030870 A1 | 2/2006 | Staudner | |
| 2006/0149302 A1 | 7/2006 | Popov | |
| 2006/0173479 A1 | 8/2006 | Smith | |
| 2006/0200095 A1 | 9/2006 | Steube | |
| 2006/0200182 A1 | 9/2006 | Prosek | |
| 2006/0282037 A1 | 12/2006 | Henderson et al. | |
| 2007/0005087 A1 | 1/2007 | Smith et al. | |
| 2007/0010842 A1 | 1/2007 | Popov | |
| 2007/0016237 A1 | 1/2007 | Smith | |

FOREIGN PATENT DOCUMENTS

| | | |
|---|---|---|
| EP | 1 997 447 A1 | 12/2008 |
| EP | 2 044 899 A2 | 4/2009 |
| JP | 2002 035001 A | 2/2002 |
| WO | WO 94/04082 | 3/1994 |
| WO | WO 02/01998 | 1/2002 |
| WO | WO 2005/023132 A2 * | 3/2005 |

OTHER PUBLICATIONS

Extended European Search Report dated Feb. 3, 2012 issued by the European Patent Office in corresponding European Patent Application No. 11 250 784.3 (3 pgs.).

Extended European Search Report completed Nov. 13, 2012 issued by the European Patent Office in European Patent Application No. 07 86 2892 (3 pgs.).

* cited by examiner

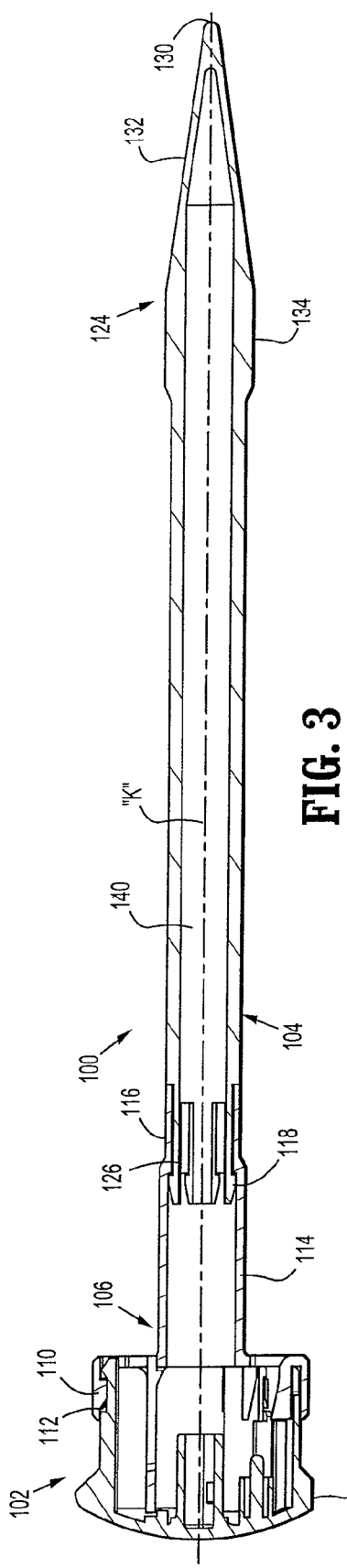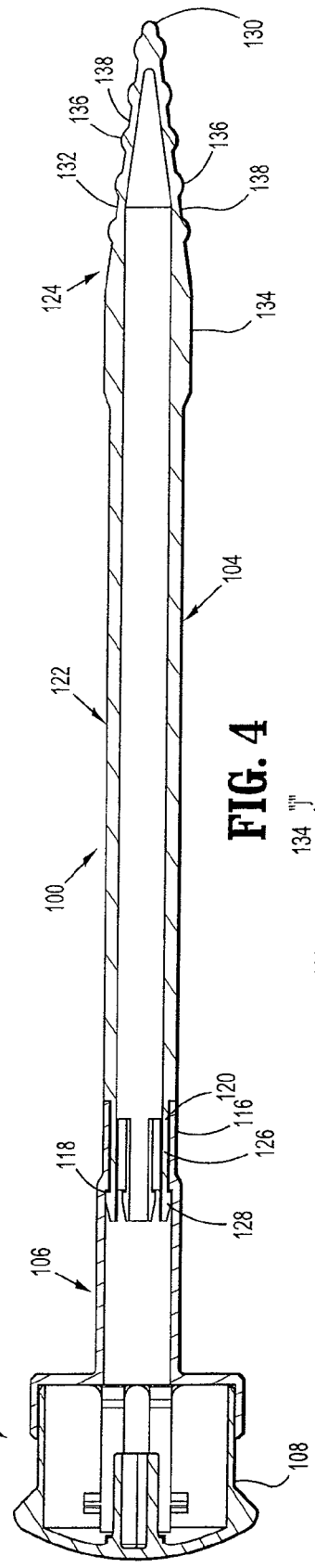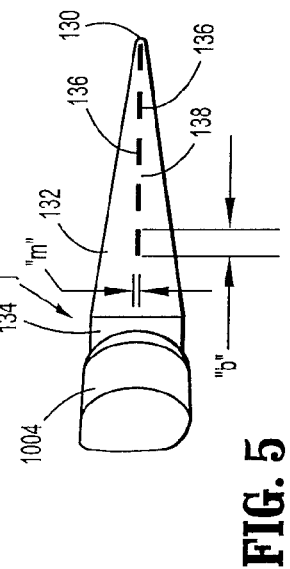

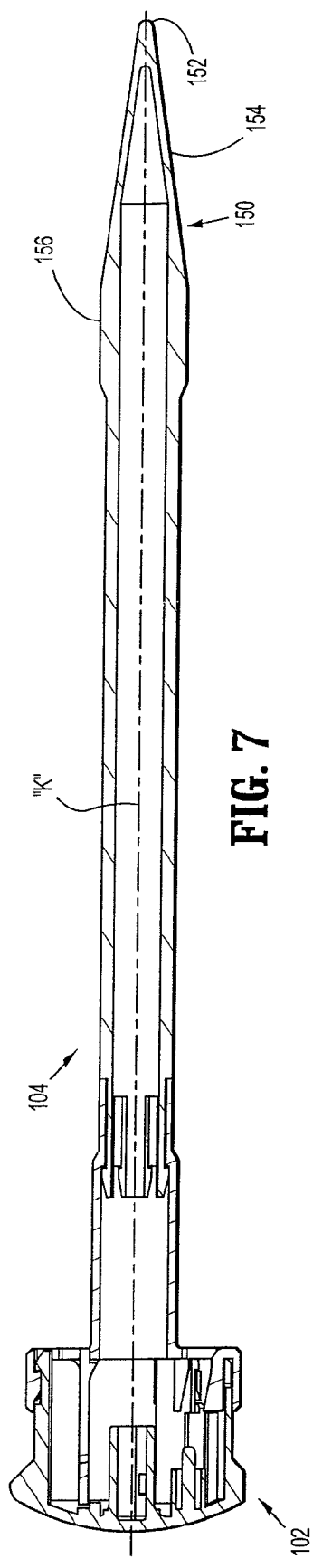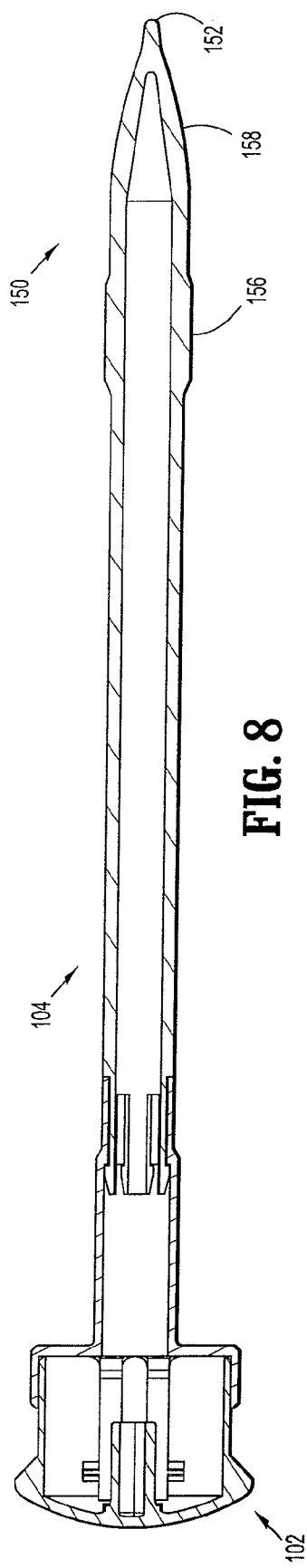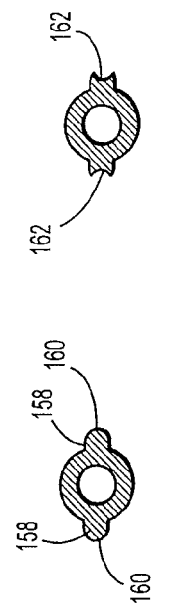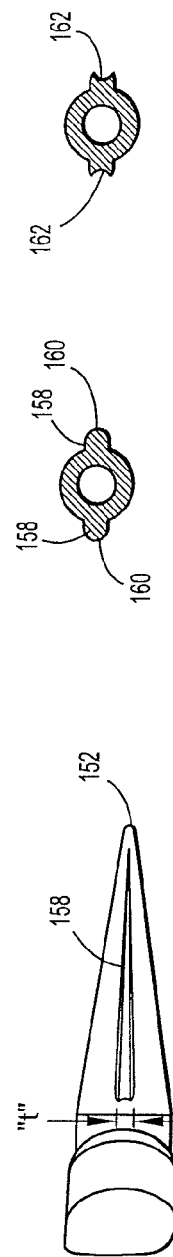

TROCAR ASSEMBLY WITH OBTURATOR DESIGN

CROSS REFERENCE TO RELATED APPLICATIONS

This application is a National Stage Application of PCT/US2007/025568 filed Dec. 14, 1007 under 35 USC §371(a), which claims priority of U.S. Provisional Patent Application Ser. No. 60/875,151 filed Dec. 15, 2006 the entire contents of which are hereby incorporated by reference.

BACKGROUND

1. Technical Field

The present disclosure relates to a trocar assembly for use in minimally invasive surgical procedures, such as endoscopic or laparoscopic type procedures.

2. Background of the Related Art

Minimally invasive procedures are continually increasing in number and variation. Forming a relatively small diameter temporary pathway to the surgical site is a key feature of most minimally invasive surgical procedures. The most common method of providing such a pathway is by inserting a trocar assembly through the skin. In many procedures, the trocar assembly is inserted into an insufflated body cavity of a patient. In such procedures, the trocar assemblies with seal mechanisms are utilized to provide the necessary pathway to the surgical site while minimizing leakage of insufflation gases.

Trocar assemblies typically include an obturator which is removably inserted through a cannula. The obturator may incorporate a sharpened or bladed penetrating end which pierces the abdominal wall during insertion of the trocar assembly. The obturator is then removed and instrument(s) are passed through the cannula to perform the desired procedure. However, in certain applications, it may be desirable to incorporate a blunt obturator as a precautionary measure to avoid piercing of underlying tissue or to perform a blunt dissection of the abdominal wall through, e.g., an existing incision.

SUMMARY

Accordingly, the present disclosure is directed to further improvements in trocar technology. In one preferred embodiment, an obturator for use in penetrating tissue includes an elongate member defining a longitudinal axis, and having a proximal end and a distal end, and a penetrating member adjacent the distal end of the elongate member. The penetrating member has a distal penetrating tip dimensioned to pass through tissue. The penetrating member defines an external wall leading toward the penetrating tip. The external wall includes a plurality of raised elements extending at least radially outwardly relative to the longitudinal axis and being in general longitudinal alignment. Adjacent raised elements are spaced along the longitudinal axis to thereby accommodate tissue displaced during passage of the penetrating member through tissue. The raised elements are dimensioned to be generally atraumatic to tissue. The raised elements may define an arcuate profile. In one embodiment, the penetrating member includes a first series of raised elements and a second series of raised elements in diametrical opposed relation to the first series of raised elements. The raised elements may be generally narrow, and may define a length along the longitudinal axis greater than a width defined along a transverse axis transverse to the longitudinal axis. In another embodiment, at least a portion of the penetrating member may be translucent. The elongate member may define an axial channel dimensioned to permit reception of a viewing device. The penetrating tip may be arcuate.

In a further embodiment, an obturator for use in penetrating tissue includes an elongate member defining a longitudinal axis, and having a proximal end and a distal end and a penetrating member adjacent the distal end of the elongate member and having a distal penetrating tip dimensioned to pass through tissue. The penetrating member defines an external wall leading to the penetrating tip. The external wall may include first and second series of raised elements arranged in diametrical opposed relation. The raised elements of each series are arranged in spaced relation along the longitudinal axis whereby spaced regions are defined between adjacent raised elements to accommodate tissue displaced during passage of the penetrating member through tissue. The raised elements may each define an arcuate profile. The raised elements may be generally narrow, and define a length along the longitudinal axis greater than a width defined along a transverse axis transverse to the longitudinal axis.

In another embodiment, an obturator for use in penetrating tissue includes an elongate member defining a longitudinal axis, and having a proximal end and a distal end and a penetrating member adjacent the distal end of the elongate member and having a distal penetrating tip dimensioned to pass through tissue. The penetrating member defines an external wall leading toward the penetrating tip. The external wall includes first and second continuous raised elements arranged in diametrical opposed relation. Each raised elements has a length relative to the longitudinal axis substantially greater than a width relative to a transverse axis transverse to the longitudinal axis. Each raised element may define a substantially arcuate profile. Each raised element may define a generally concave outer surface. The width of each of the first and second raised elements defined along the transverse axis increases from distal to proximal.

BRIEF DESCRIPTION OF THE DRAWINGS

Preferred embodiments of the present disclosure are described hereinbelow with references to the drawings, wherein:

FIG. 3 is a first side cross-sectional view of the obturator assembly of the trocar assembly;

FIG. 4 is a second cross-sectional view of the obturator assembly;

FIG. 5 is a side plan view of the penetrating end of the obturator assembly;

FIG. 7 is a first side cross-sectional view of the obturator assembly of FIG. 6;

FIG. 8 is a second cross-sectional view of the obturator assembly of FIG. 6;

FIG. 9 is a side plan view of the penetrating end of the obturator assembly of FIG. 6;

FIG. 10 is a cross-sectional view of the penetrating end of the obturator assembly taken along the lines 10-10 of FIG. 9; and FIG. 11 is a view similar to the view of FIG. 1 illustrating an alternate embodiment of the penetrating end.

DETAIL DESCRIPTION OF PREFERRED EMBODIMENTS

Figure 1:
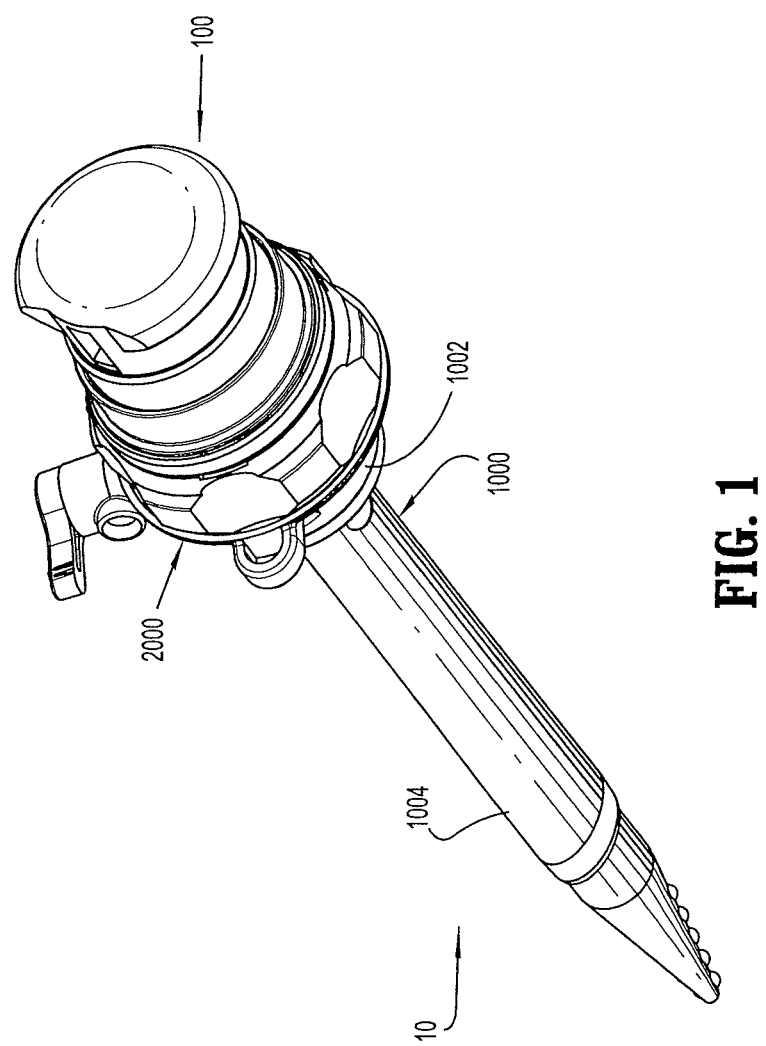
FIG. 1 is a perspective view of a trocar assembly constructed in accordance with the present disclosure illustrating a cannula assembly and an obturator assembly positioned within the cannula assembly.
Figure 2:
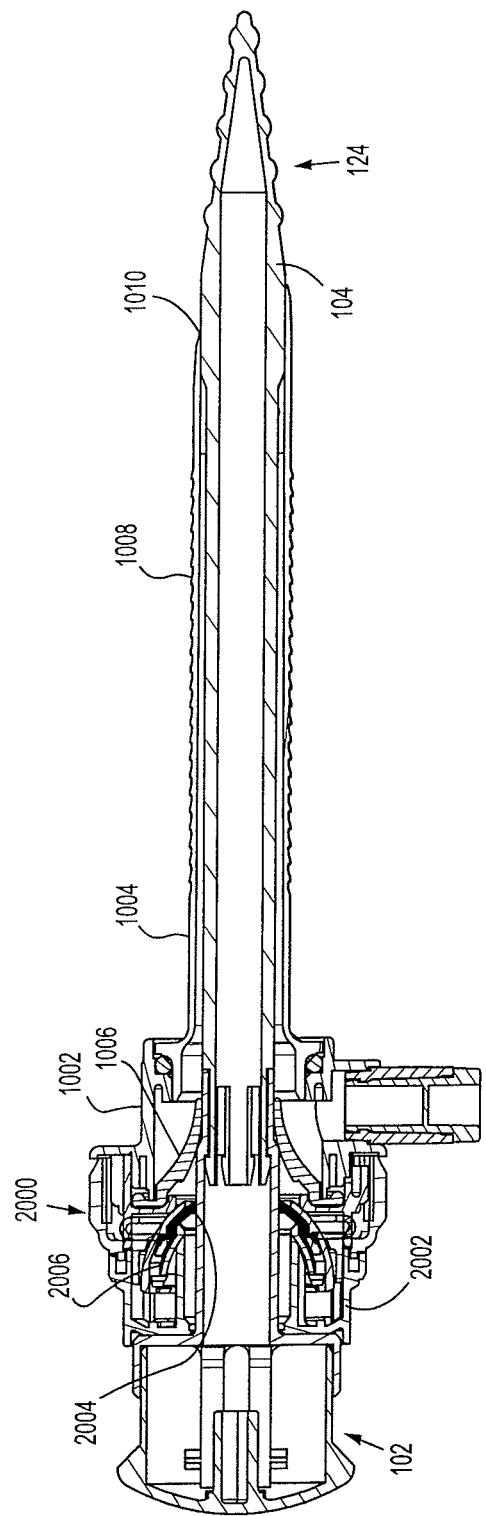
FIG. 2 is a side cross-sectional view of the trocar assembly of FIG. 1.
Figure 6:
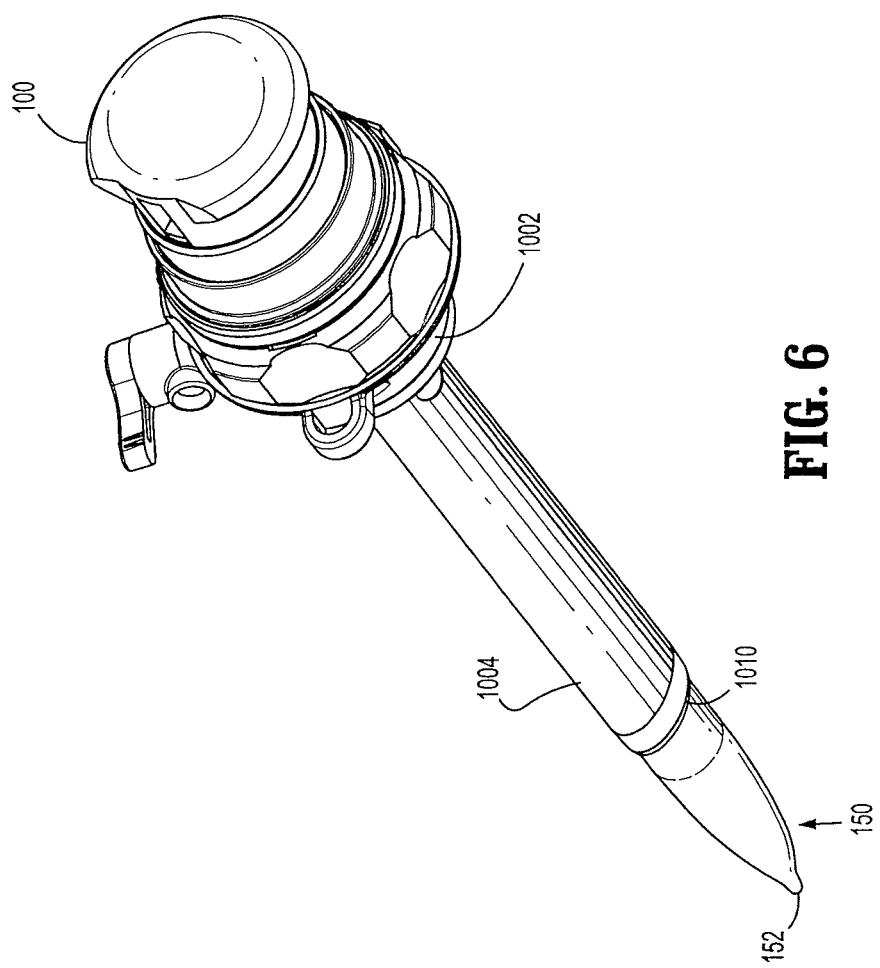
FIG. 6 is a perspective view of the trocar assembly incorporating an alternate embodiment of the obturator assembly.

Referring now in detail to the drawing figures, in which, like references numerals identify similar or identical elements, there is illustrated, in FIGS. 1 and 2, a trocar assembly constructed in accordance with a preferred embodiment of the present disclosure, and designated generally by reference numeral 10. Trocar assembly 10 is particularly adapted for use in minimally invasive surgical procedures such as endoscopic or laparoscopic procedures. Generally, trocar assembly 10 includes two principal subassemblies, namely, obturator assembly 100 and cannula assembly 1000.

Cannula assembly 1000 may be any cannula assembly suitable for use in a laparoscopic surgical procedure. In one preferred embodiment, cannula assembly 1000 includes cannula housing 1002 and cannula sleeve 1004 extending from the cannula housing 1002. Either or both cannula housing 1002 and cannula sleeve 1004 may be transparent in part or in whole and are fabricated from biocompatible metal or polymeric material. Cannula assembly 1000 may include an internal seal 1006 such as a duck-bill valve or other zero closure valve adapted to close in the absence of a surgical instrument to prevent passage of insufflation gases through the cannula assembly 1000. Cannula sleeve 1004 may include locking ribs 1008 on its external surface adapted to facilitate retention of the cannula sleeve 1004 within the tissue as shown in FIG. 2. One suitable locking rib arrangement which may be incorporated into cannula sleeve 1004 is disclosed in commonly assigned U.S. Pat. No. 6,432,085 to Stellon, issued on Aug. 13, 2002, the entire contents of which disclosure is incorporated herein in its entirety by reference. Cannula sleeve 1008 may further include beveled leading end 1010. Beveled leading end 1010 may provide advantages with respect to introduction of cannula sleeve 1004, e.g., including a reduction in the insertion force into tissue when the assembled surgical trocar assembly is inserted into tissue. For example, the beveled characteristic reduces the profile of leading end 1010 of cannula sleeve 104 to facilitate initial entry into, and passage through, the tissue. It is envisioned that leading end 1010 may encompass a single linear surface or may be arcuate in nature having a predetermined radius of curvature. As a further alternative, leading end 1010 may include a compound curve surface incorporating at least two radii of curvature. Other arrangements are also envisioned.

Trocar assembly 10 may also include a seal assembly 2000 which is preferably releasably mounted to cannula housing 1002. Means for releasably connecting seal assembly 2000 to cannula housing 1002 may include a bayonet coupling, threaded connection, latch, friction fit, tongue and groove arrangements, snap-fit, etc. Seal assembly 2000 includes seal housing 2002 and at least one internal seal 2004 which is adapted to form a fluid tight seal about an instrument inserted through the seal assembly 2000. One suitable seal may be the fabric seal disclosed in commonly assigned U.S. Pat. No. 6,702,787 to Racenet, issued Mar. 9, 2004, the entire contents of which are incorporated herein by reference. The seal disclosed in the '787 patent may be a seal having a first layer of resilient material and a second fabric layer juxtaposed relative to the first layer. Further details of the seal may be ascertained by reference to the '787 patent. Seal assembly 2000 may or may not be a component of cannula assembly 1000. For example, the seal assembly may be a separate, removable assembly. In the alternative, the seal assembly may comprise an integral part of the cannula assembly 1000 and not be removable.

Preferably, seal assembly includes seal housing 2002 defining a longitudinal opening to permit passage of instrumentation through the seal housing 2002 and gimbal mount 2006 disposed within the seal housing 2002. Gimbal mount 2006 houses seal 2002. Gimbal mount 2006 is adapted for angular movement relative to the central longitudinal axis of seal housing 2002 upon angulation of the surgical instrument while seal 2002 substantially maintains a sealed reception about a surgical instrument introduced through the seal 2002. This gimbal arrangement is disclosed in commonly assigned U.S. patent application Ser. No. 11/069,098, filed Mar. 1, 2005 to Smith et al., which is a continuation-in-part application of commonly assigned U.S. patent application Ser. No. 10/264,556, filed Oct. 4, 2002 to Smith et al., the entire contents of each application being incorporated herein by reference.

With reference now to FIGS. 3-5, in conjunction with FIG. 2, obturator assembly 100 will be discussed. Obturator assembly 100 includes obturator housing 102 and obturator member 104 extending distally from the housing 102. Obturator member 104 defines obturator axis "k". Obturator housing 102 includes housing base 106 and housing cover 108. Housing base 106 may be attached to housing cover 108 by engaging mating surfaces, for example, by resilient latches 110 of housing base 106 interlocking with correspondingly dimensioned latch recesses 112 on the exterior of housing cover 108. Preferably, to uniformly connect housing base 106 and housing cover 108 at least two corresponding latches 110 and recesses 112 are spaced evenly around the peripheral areas of the housing base 106 and the housing cover 108, respectively. Alternatively, housing base 106 and housing cover 108 may be a single monolithically formed unit. Housing base 106 of obturator housing 102 defines base extension 114 which connects to obturator member 104. Base extension 114 defines leading end 116 having a reduced dimension or diameter. This reduction in diameter of base extension 114 defines internal ledge or shelf 118. Preferably, obturator housing 102 is configured and dimensioned to functionally cooperate with cannula assemblies 1000 that range in size, e.g., from about 5 mm to about 15 mm in diameter.

Obturator member 104 defines trailing or proximal end 120, intermediate shaft 122 and leading or distal penetrating end 124. Proximal end 120 includes a plurality of, e.g., four locking tabs 126. Locking tabs 126 each include locking detents 128 which depend radially outwardly relative to longitudinal axis "k". Locking detents 128 engage internal locking shelf 118 of base extension 114 in snap relation therewith to connect obturator member 104 to obturator housing 102. As to be appreciated, locking tabs 126 initially may deflect inwardly upon positioning of proximal end 116 of obturator member 104 within leading end 116 of base extension 114 whereby, upon clearing of internal shelf 118, the locking tabs 126 assume there initial positions with locking detents 128 engaging the internal shelf 118. Other means for connecting obturator housing 102 and obturator member 104 are also envisioned such as with the use of cements, threaded couplings, etc. In the alternative, obturator housing 102 and obturator member 104 may be a single monolithic unit.

With reference to FIGS. 3-5, in conjunction with FIG. 1, leading penetrating end 124 of obturator member 104 includes leading tip 130 and tapered or frusto-conical portion 132 extending proximally from leading tip 130 and terminating in cylindrical portion 134. Leading tip 130 is preferable rounded or arcuate in configuration to define a blunt axial profile as shown. Frusto-conical portion 132 tapers outwardly from leading tip 130 in a linear manner to cylindrical portion 132. Frusto-conical portion 132 further defines a plurality of raised elements, protrusions or convexities 136 extending along its outer surface and radially outwardly relative to longitudinal axis "k". Raised elements 136 are relatively thin in width as best shown in FIG. 5 defining a width "m" along a transverse axis "j" substantially less than a length "b" (FIG. 5) along the longitudinal axis "k". Raised elements 136 are generally aligned with themselves relative to longitudinal axis "k" with adjacent raised elements 136 in spaced relation to define relief areas 138. The spacing between adjacent raised elements 136 may be constant or, alternatively, may vary along the longitudinal axis "k" as desired. Preferably, first and second series of raised elements 136 are provided with the series being disposed in diametrical opposed relation as best depicted in FIG. 4.

Raised elements 136 provide a penetrating function which is not as traumatic as a linear obturator blade but greater than a purely blunt obturator. Moreover, the relatively thin arrangement of raised elements 136 may provide on incising capability or may be configured to be atraumatic. Relief areas 138 accommodate tissue which may be displaced during penetration of leading penetrating end 124 thereby facilitating passage through tissue. Cylindrical portion 134 defines a diameter which generally approximates the diameter of cannula sleeve 1008 to facilitate at least initial passage of the cannula sleeve 1008 through tissue.

Obturator member 104 may define an axial channel 140 to permit insertion of an instrument for viewing capabilities if desired. With this arrangement, at least leading penetrating end 124 of obturator member 104 could be translucent or transparent. An opening or channel could be provided within obturator housing 102 to permit passage of the instrument.

Referring now to FIGS. 6-10, there illustrated an alternate embodiment of the obturator assembly for use with trocar assembly 10. Obturator assembly 150 is substantially similar to the obturator assembly 100 of FIG. 1. However, in accordance with this embodiment, leading penetrating end 150 includes leading tip 152, frusto-conical portion 154 extending from the leading tip 152 and cylindrical portion 156. Leading tip 152 is preferably arcuate in configuration. Frusto-conical portion 154 includes a pair of diametrically opposed penetrating raised elements or ribs 158. Raised elements 158 are spaced from leading tip 152 and extend in a general axial direction as shown. Raised elements 158 each define a width "t" as measured relative to transverse axis "j" which gradually or linearly increases from distal to proximal. Outer surfaces 160 of raised elements 158 are preferably convex or arcuate in configuration as best depicted in FIG. 10. Raised elements 158 provide a less traumatic piercing action relative to bladed obturators, but, exhibit greater piercing capabilities than a blunt obturator. The tapering affect of raised elements is 158 presents a reduced profile upon initial entry of leading penetrating end 150 whereby upon continued entry the larger width area of the raised elements 158 pierce or penetrate the tissue to enlarge the opening in the tissue. In an alternate configuration depicted in FIG. 11, raised elements 158 define concave outer surfaces 162. This arrangement provides a hollow ground effect which provides enhanced passage through tissue.

Except where noted otherwise, the materials utilized in the components of the presently disclosed trocar assembly generally include materials such as, for example, ABS, polycarbonate, stainless steel, titanium and any other suitable biocompatible metals and/or polymeric materials. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An obturator for use in penetrating tissue, which comprises:
    an elongate member defining a longitudinal axis, and having a proximal end and a distal end; and
    a penetrating member adjacent the distal end of the elongate member and having a distal penetrating tip dimensioned to pass through tissue, the penetrating member defining a tapered portion leading toward the penetrating tip, the tapered portion including a plurality of raised elements extending at least radially outwardly relative to the longitudinal axis and being in general longitudinal alignment, adjacent raised elements being longitudinally spaced along the longitudinal axis to thereby accommodate tissue displaced during passage of the penetrating member through tissue, the raised elements being configured and dimensioned to be generally atraumatic to tissue, and being substantially identical in configuration and dimensions, the raised elements being generally narrow and defining a length extending along and linearly aligned with the longitudinal axis greater than a width defined along a transverse axis transverse to the longitudinal axis.

2. The obturator according to claim 1 wherein the raised elements define an arcuate profile.

3. The obturator according to claim 1 including a first series of longitudinally spaced raised elements with each of the raised elements of the first series being in general longitudinal alignment and a second series of longitudinally spaced raised elements with each of the raised elements of the second series being in general longitudinal alignment, the first series of raised elements being in diametrical opposed relation to the second series of raised elements.

4. The obturator according to claim 1 wherein at least a portion of the penetrating member is translucent.

5. The obturator according to claim 4 wherein the elongate member defines an axial channel dimensioned to permit reception of a viewing device.

6. The obturator according to claim 1 wherein the penetrating tip is arcuate.

7. The obturator according to claim 1 wherein the spacing between adjacent raised elements is constant.

8. The obturator according to claim 1 wherein the spacing between adjacent raised elements varies along the longitudinal axis.

9. The obturator according to claim 1 including a first series of longitudinally spaced raised elements with each of the raised elements of the first series being in general longitudinal alignment and a second series of longitudinally spaced raised elements with each of the raised elements of the second series being in general longitudinal alignment.

10. An obturator for use in penetrating tissue, which comprises:
   an elongate member defining a longitudinal axis, and having a proximal end and a distal end; and
   a penetrating member adjacent the distal end of the elongate member and having a distal penetrating tip dimensioned to pass through tissue, the penetrating member defining a tapered portion leading to the penetrating tip, the tapered portion including first and second series of raised elements arranged in diametrical opposed relation, the raised elements of each series being arranged in longitudinal spaced relation along the longitudinal axis whereby spaced regions are defined between adjacent raised elements of each series to accommodate tissue displaced during passage of the penetrating member through tissue, the raised elements being generally narrow, defining a length along and linearly aligned with the longitudinal axis greater than a width defined along a transverse axis transverse to the longitudinal axis, being configured and dimensioned to be generally atraumatic to tissue, and being substantially identical in configuration and dimensions.

11. The obturator according to claim 10 wherein the raised elements each define an arcuate profile.

12. An obturator for use in penetrating tissue, which comprises:
   an elongate member defining a longitudinal axis, and having a proximal end and a distal end; and
   a penetrating member adjacent the distal end of the elongate member and having a distal penetrating tip dimensioned to pass through tissue, the penetrating member defining a tapered portion leading toward the penetrating tip, the tapered portion including first and second continuous raised elements arranged in diametrical opposed relation, each raised element having a length relative to the longitudinal axis substantially greater than a width relative to a transverse axis transverse to the longitudinal axis, each raised element defining a generally concave channel in an outer surface thereof and extending longitudinally between a proximal and a distal end thereof, the raised elements being configured and dimensioned to be generally atraumatic to tissue, and being substantially identical in configuration and dimensions.

13. The obturator according to claim 12 wherein the width of each of the first and second raised elements defined along the transverse axis increases from distal to proximal.

14. The obturator according to claim 12 wherein the raised elements are spaced from the penetrating tip.

15. An obturator for use in penetrating tissue, which comprises:
   an elongate member defining a longitudinal axis, and having a proximal end and a distal end; and
   a penetrating member adjacent the distal end of the elongate member configured and dimensioned to pass through tissue, the penetrating member defining a tapered portion including a plurality of raised elements each defining a width extending along an axis transverse in relation to the longitudinal axis, and a length extending along and linearly aligned with the longitudinal axis, the width being less than the length, the raised elements being configured and dimensioned to be generally atraumatic to tissue, and being spaced along the longitudinal axis to thereby accommodate tissue displaced during passage of the penetrating member through tissue.

16. The obturator according to claim 15, wherein the raised elements are arranged into a first series and a second series positioned in diametrical opposition.

17. The obturator according to claim 16, wherein each of the raised elements comprising the first series are in general longitudinal alignment, and each of the raised elements comprising the second series are in general longitudinal alignment.

18. The obturator according to claim 15, wherein the raised elements extend radially outwardly relative to the longitudinal axis.

19. The obturator according to claim 15, each of the raised elements defines a generally concave outer surface.

20. The obturator according to claim 15, wherein each of the raised elements is substantially identical in configuration and dimensions.

21. An obturator for use in penetrating tissue, which comprises:
   an elongate member defining a longitudinal axis, and having a proximal end and a distal end; and
   a penetrating member adjacent the distal end of the elongate member configured and dimensioned to pass through tissue, the penetrating member defining a tapered portion including a generally smooth surface interrupted circumferentially by a plurality of raised elements, the raised elements being configured and dimensioned to be generally atraumatic to tissue, and being spaced along the longitudinal axis to thereby accommodate tissue displaced during passage of the penetrating member through tissue, the raised elements being generally narrow and defining a length extending along and linearly aligned with the longitudinal axis greater than a width defined along a transverse axis transverse to the longitudinal axis.

22. The obturator according to claim 21, wherein the raised elements are arranged into a first series and a second series positioned in diametrical opposition.

23. The obturator according to claim 22, wherein each of the raised elements comprising the first series are in general longitudinal alignment, and each of the raised elements comprising the second series are in general longitudinal alignment.

24. The obturator according to claim 21, wherein the raised elements extend radially outwardly relative to the longitudinal axis.

25. The obturator according to claim 21, each of the raised elements defines a generally concave outer surface.

26. The obturator according to claim 21, wherein each of the raised elements is substantially identical in configuration and dimensions.

* * * * *